United States Patent [19]

Grosskopf

[11] 4,047,205
[45] Sept. 6, 1977

[54] METHOD AND MEANS FOR MEASURING SUBSTANCE VOLUMES IN LIGHT-TRANSMITTING SAMPLES

[75] Inventor: Rudolf Grosskopf, Koenigsbronn, Germany

[73] Assignee: Carl Zeiss-Stiftung, Oberkochen, Wurttemberg, Germany

[21] Appl. No.: 674,841

[22] Filed: Apr. 7, 1976

[30] Foreign Application Priority Data

Apr. 9, 1975 Germany .............................. 2515513

[51] Int. Cl.² .............................................. H04N 7/18
[52] U.S. Cl. ................................. 358/107; 235/92 MT
[58] Field of Search .................. 358/107; 235/92 PC, 235/92 MT

[56] References Cited

U.S. PATENT DOCUMENTS

| 3,967,053 | 6/1976 | Grosskopf | 235/92 PC |
| 3,980,812 | 9/1976 | Grosskopf | 358/107 |

*Primary Examiner*—Howard W. Britton
*Attorney, Agent, or Firm*—Hopgood, Calimafde, Kalil, Blaustein & Lieberman

[57] ABSTRACT

The invention contemplates an improved method and means of electronic-image analysis within a field of raster-scanned subject matter, wherein the volume of an object is evaluated according to its observed light-absorbing properties. The evaluation progresses as successive scans of the object area, at progressively quantized levels of transmitted light, and an appropriate calibration factor is applied to each of the successive object areas thus scanned, so that a volume measurement results from summing the calibration-corrected areas.

12 Claims, 6 Drawing Figures

METHOD AND MEANS FOR MEASURING SUBSTANCE VOLUMES IN LIGHT-TRANSMITTING SAMPLES

This invention relates to a method and means for measuring substance volumes in light-transmitting samples within a raster-scanned field.

In prior-art methods of quantitative image analysis, an image such as a microscopically produced image is scanned in a raster pattern by means of a focused beam, for which a beam of light or an electron beam may be used. Commonly, the scanning beam of a television camera system is used, for its speed and convenience. Scan-derived video signals are fed to a discriminator which selects the objects to be evaluated, on the basis of preselected criteria. The discriminator supplies binary signals whose length corresponds to the scan distance of the scanning beam within the selected objects. Finally, these signals are fed to an evaluation unit which measures therefrom the values to be determined, for instance, the number of objects, their surface area or their extent in a predetermined direction. In certain applications of quantitative image analysis, as when evaluating biological samples, one is confronted with the need to measure the substance volume of an analyzed sample. This is possible by observing light-transmission and/or light-absorption of the sample, using the law of Lambert-Beer, namely, substance volume is proportional to the logarithm of the light absorption when using monochromatic light.

However, the application of this law in the case of commonly available samples with non-uniform distribution of the substance leads to great difficulties. Due to the logarithmic relation between light signal and substance volume, a logarithmic conversion of the measuring signal is required for each individual image point, and an integration to determine substance volume is possible only after this logarithmic converstion. This requirement dictates complexity of apparatus, since a logarithmic converter in a television scanning system must operate at 5 megaHertz, for compatability with German standards.

It is, accordingly, an object of the invention to provide an improved volume-measuring method and means for sample evaluations of the character indicated. Specifically, it is an object to provide for such volume evaluation, in a raster-scanned field, with a substantial economy of apparatus and with reliability of measurement.

In performing the method of the invention, the sample is evaluated by viewing in a succession of steps, each of which involves a frame scan and thus the development of a surface area of the sample, and at each step the surface area is measured for a given quantized level or region of light absorption (between preselected limits); each of these areas is then subjected to an appropriate calibration correction, before addition to complete the volume evaluation.

In the new method, each of the area-scan steps produces a contour envelope for each of the individual sample areas, and each such contour is characterized by lines of equal density, so-called "equi-densities". Each surface area (contour envelope) is associated with a preselected density which is defined by a determined light absorption. After the surface measurement has been effected, the obtained values are logarithmated, i.e., logarithimically converted or processed. Thus, what heretofore had to be a logarithmation of the signal from each image point is now replaced by logarithmation of area signals. Such area signals are generated at relatively low frequency, e.g., at frame-repetition frequency for a TV-scan situation, so that a simple logarithmating device can be used, while the rest of the circuit can be composed of circuit elements commonly used in quantitative image analysis.

If the differences between quantized levels of light absorption for successive surface areas are selected as appropriate for a given measuring problem, the desired substance volume will be measured with great accuracy even though the measuring apparatus is of relatively simple design.

If the samples to be evaluated are such that the law of Lambert-Beer applies, the logarithm of the associated mean light absorption may be used as the calibrating value for each surface area. However, the novel method is not limited to such samples since it also enables the application of functions other than logarithmic evaluation functions. Such an evaluation or calibrating function can be determined anew, from case to case, without requiring a change in the electronic circuit.

In the novel method, the sample is scanned in a raster pattern, and the resulting video signal is subjected to a discrimination increasing in quantized steps by equal amounts in the direction of increasing gray values; at each step, the surface corresponding to the transmitted signal is measured and is subtracted from the surface measured during the preceding step.

Thus, starting from a pre-selected gray value, the first raster scan of the imaged field involves measurement of the surface of all areas which show at least this gray value. During succeeding steps, the measured surface becomes increasingly smaller, as gray value increases. By taking the difference between measured areas for particular adjacent steps, a partial-surface area measurement is obtained for an associated pre-selected gray-value range. The partial surfaces thus measured are multiplied by a calibrating value, for instance, the logarithm of the associated mean light absorption; the resulting partial products are added, and the sum signal is supplied as measuring signal.

Discrimination of the video signal is effected by means of a discriminator whose threshold value is adjusted in accordance with a predetermined program, in steps, by preselected amounts. The signal thus discriminated is fed to an integrator. The output signal of the integrator is fed to an evaluation unit which carries out all necessary further difference-, product-, and sum formations, and which also controls the adjustment of the threshold value of said discriminator.

The invention will now be described more fully by reference to the accompanying drawings, in which.

Figure 1:
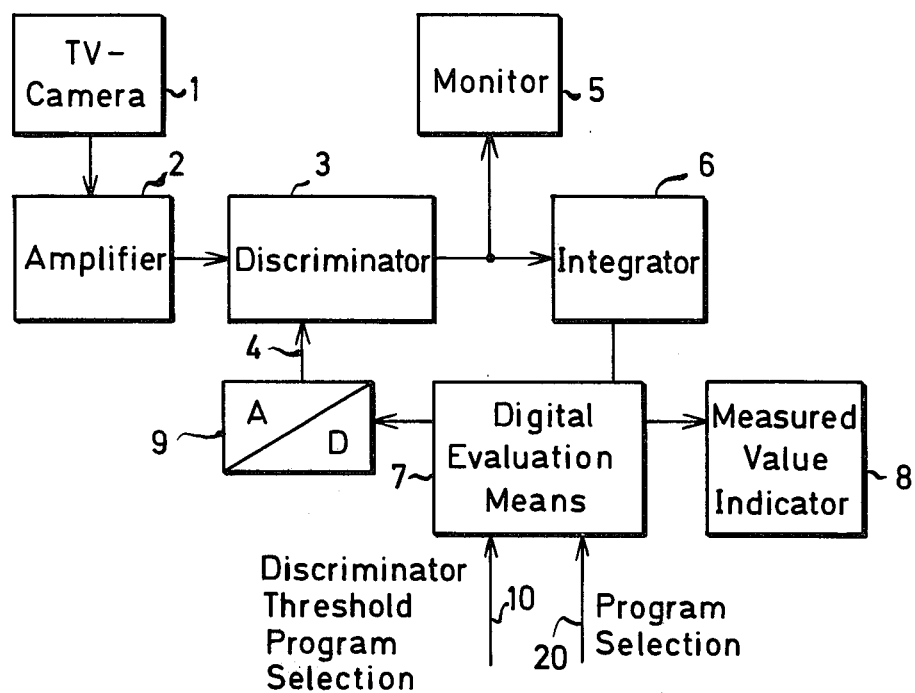
FIG. 1 is an electrical block diagram schematically illustrating an arrangement of the invention in which the total image field is evaluated.

In FIG. 1, reference numeral 1 designates a television camera which serves to scan a light-transmitting sample, such as the microscopically produced image of a biological sample. The video signal produced by this camera is fed to an amplifier 2 and from there to a discriminator 3. The latter generates a logic H-signal at its output when the video signal is below a threshold value preset via line 4, and a logic L-signal when the video signal is above this threshold. The length of the H-signal generated by the discriminator corresponds to the distance which the scanning beam of the camera 1 moves within the selected image object. The discriminated signal is supplied to a monitor 5 on the display screen of which the selected objects appear with uniform gray color. From the discriminator 3 the signal is also supplied to an integrator 6 which adds up all H-signals for each image scan or frame. The sum signal corresponding to the total surface of the objects selected by the discriminator 3 passes from the integrator 6 to a digital evaluating unit 7. Therein, the signal is processed further in a manner still to be described and finally passes to a measured-value indicator 8.

Threshold-value shifting at discriminator 3 for the next-succeeding frame is controlled by a connection 4 from the digital-evaluation unit 7, via a digital-to-analog converter 9. The position of the threshold value at the beginning of measurement and the distance between two successive threshold values are matters of selection, being present in the digital evaluation unit 7, as at 10.

Figure 3:
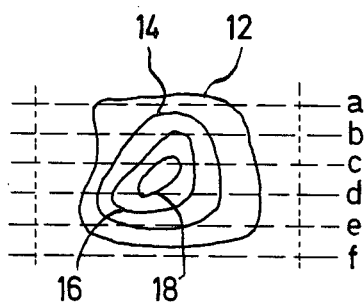
FIG. 3 illustrates an object to be evaluated in the scanning field.

The function of the arrangement shown in FIG. 1 will now be described more fully by reference to FIGS. 3 and 4. And for simplification, FIG. 3 illustrates a particle to be evaluated in the indicated scanning field, the simplification being through use of only six scanning lines a, b, c, d, e, f. Also for simplification, it is assumed that only a single particle is contained in the total image field in FIG. 3. The video signal produced when this particle is scanned, is illustrated in FIG. 4.

Figure 4:
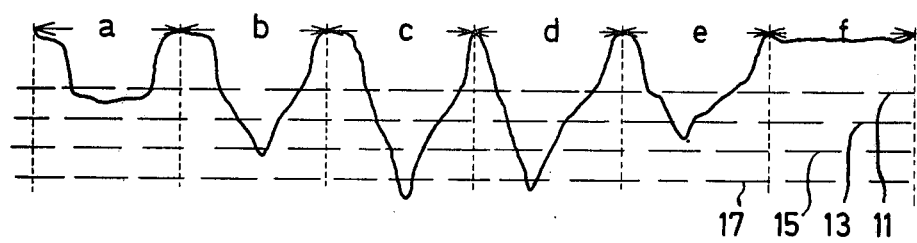
FIG. 4 illustrates the video signal generated during scanning of the object according to FIG. 3.

First, an image scan takes place in which, based on the input threshold level selection at 10, the digital evaluation unit 7 has adjusted the threshold value of the discriminator 3 according to the line 11 in FIG. 4, via the digital-to-analog converter 9. All signal levels below line 11 supply a logic H-signal at the output of discriminator 3. Thus, on the screen of monitor 5, a particle is seen which is limited by the contour line or envelope 12 (FIG. 3), while the digital evaluation unit 7 is supplied by the integrator 6 with a signal corresponding to the scanned surface of the particle limited by and between intercepts of the contour line 12. During the next area-scan step, the setting of the discriminator threshold is adjusted by the evaluation unit 7 (via converter 9) in such a manner as is shown in FIG. 4 by line 13; correspondingly, on the screen of monitor 5 a particle appears which is limited by the smaller contour line 14, and the surface area of this particle corresponds to the sum signal now supplied to the evaluation unit 7.

The evaluation unit 7 develops the difference between the integrated first and the second surface signals, i.e., it defines the quantized-density surface located between the boundary lines (contour lines of equal density) 12 and 14 in FIG. 3. At the same time, the area of this quantized-density is multiplied by the logarithm of the light absorption which corresponds to the mean value between the thresholds 11 and 13; alternatively, instead of this logarithmic value, another calibrating value or function can be used for multiplication, the particular function being contained in the program supplied to the evaluation unit 7, as suggested at 20.

The product of area enclosed by the lines of equal density 12-14 times the associated calibrating value is stored in the evaluation unit 7. For the next step, according to the program supplied to the evaluation unit 7 via line 20, unit 7 adjusts via converter 9 the discriminator threshold a further step in the direction towards higher gray values for a distance preset via line 10, the new threshold value being indicated by line 15 in FIG. 4; and, on the screen of monitor 5, a particle appears which is enclosed by the contour line 16. At the same time, the evaluation unit 7 ascertains the difference area between adjacent equal-density contour lines 14–16 and computes the product of this area, times the associated calibrating value. In the next-succeeding step, the evaluation unit 7 adjusts the discriminator threshold according to line 17 in FIG. 4, and the particle thereupon shown at monitor 5 is enclosed by the contour line 18. After calculating the product of area enclosed by the contour lines of equal density 16-18, times the associated calibrating value, the evaluation unit also calculates the product of area enclosed by the line of equal density 18, times the associated calibrating value. The successive products thus formed and stored are finally added within the evaluation means 7, and the resulting sum signal is indicated as at 8. This sum signal indicates directly and digitally the desired substance volume within the object illustrated in FIG. 3.

Figure 2:
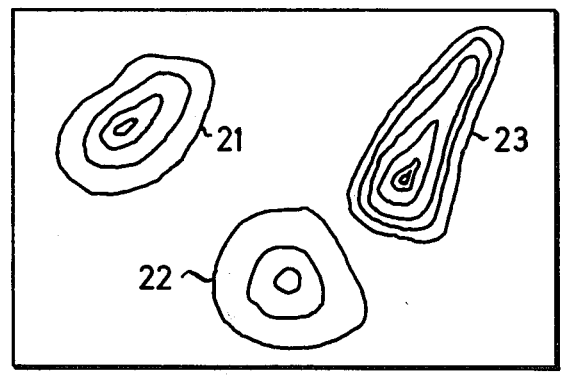
FIG. 2 illustrates an image field containing objects or particles to be evaluated by means of the arrangement of FIG. 1.

FIG. 2 illustrates an image field containing several objects 21, 22, 23, during analysis by the arrangement and technique of FIG. 1. Different lines of equal density can be recognized, corresponding to the lines 12, 14, 16, 18 of FIG. 3, the same being formed in the course of the measuring process. In the illustrated embodiment, the measured value indication 8 indicates directly the total substance volume of all the objects 21, 22, 23 contained in the image field.

Figure 5:
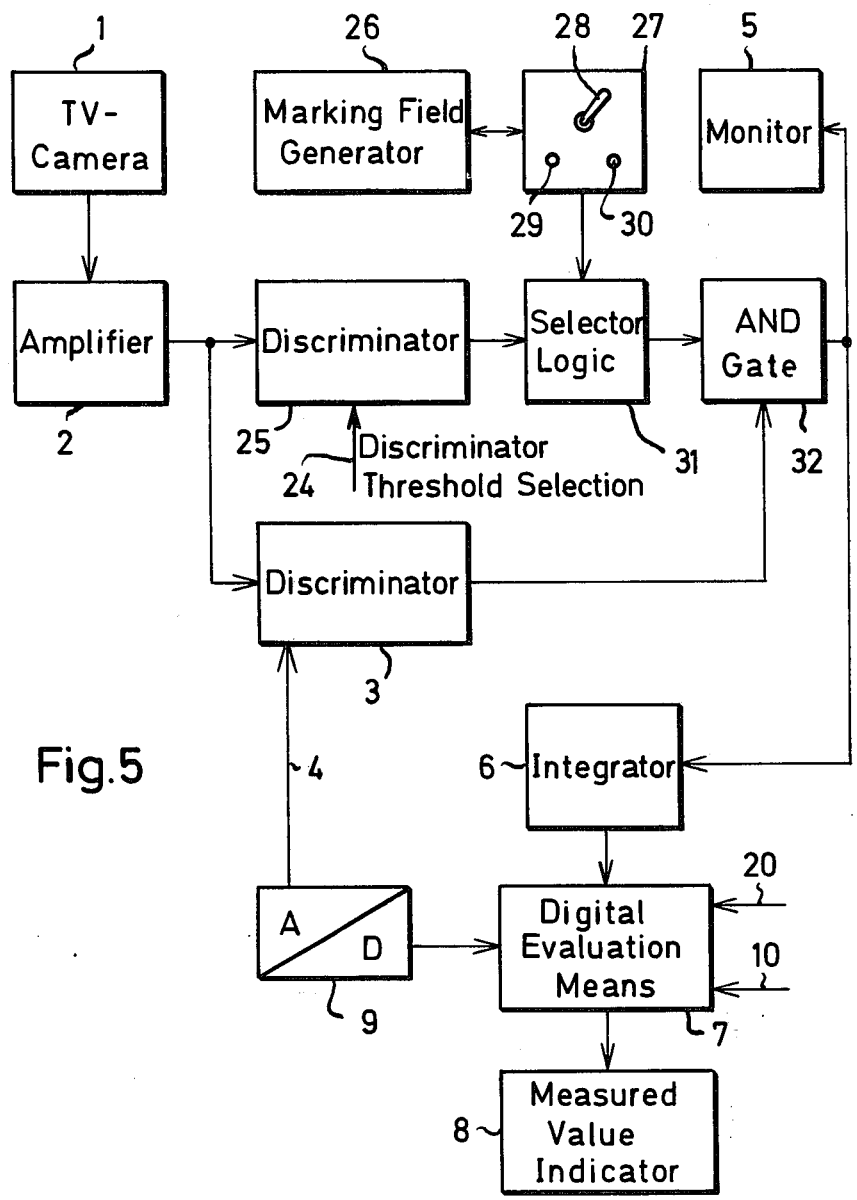
FIG. 5 illustrates another arrangement in which individual objects within an image field can be selected for the analysis.

FIG. 5 illustrates an arrangement which makes it possible to select individual objects for evaluation in an image field containing plural objects. Such an image field is shown, for instance, in FIG. 6. In addition to the discriminator 3, the arrangement of FIG. 5 includes another discriminator 25 whose threshold value is adjustable, as suggested at 24. The output signal of the amplifier 2 is supplied both to the discriminator 25 and to the discriminator 3. The discriminator 25 serves to select a specific quantity of objects from an image field whose gray value exceeds the threshold value adjusted as at 24.

Reference numeral 26 designates a marking-field generator whose voltage is supplied to an arrangement 27. The latter has a control stick 28 by which a limited-area pulse field, with width and height adjustable by means of knobs 29 and 30, can be moved across the whole image field. The thus-selected pulse field appears on monitor 5 as a bright rectangle, and the synchronizing coordinate signals therefor are supplied to a selector logic (or search-signal generator) 31 which may be as described and illustrated in detail in copending Grosskopf, et al. patent Application (now U.S. Pat. No. 3,980,812) Ser. No. 542,012. The output voltage of the selector logic 31 and the output voltage of the discriminator 3 are supplied to an AND-gate 32. Gate 32 allows marking-field generated signals to pass to monitor 5 and to the integrator 6 as soon as they exceed the threshold values of the discriminators 3 and 25, all pursuant to selection via control means 26, 27, 31.

Figure 6:
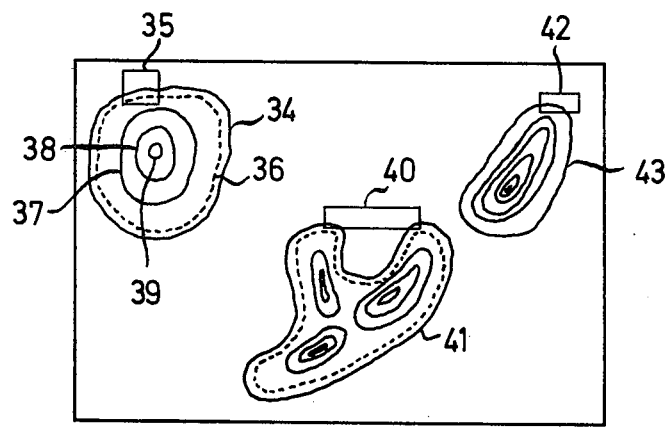
FIG. 6 illustrates an image field evaluated by the arrangement of FIG. 5.

FIG. 6 illustrates an image field being analyzed by means of the arrangement of FIG. 5. First, the threshold value of discriminator 25 is adjusted at 24 in such manner that only objects are contained in the image field whose gray value exceeds the preset value. One of these objects is referenced 34, within which the line of equal density corresponding to the selected threshold value of discriminator 25 is referenced 36. By means of the digital evaluation unit 7 and of the digital-to-analog converter 9, the lines of equal density 37, 38, 39 are successively formed, as already described in greater detail by reference to FIG. 1. Evaluation of the object 34 is effected as soon as the pulse field 35 (generated as at 26, 27) intersects the object 34. In such case, the AND-gate 32 supplies signals to the integrator 6 which are evaluated in a manner similar to that described in connection with FIGS. 1, 3 and 4.

After evaluation of the object 34 in FIG. 6 the length and width of the pulse field is, for instance, readjusted by means of the knobs 29 and 30 and is shifted by manual operation of the control stick 28 such that it intersects the display of another object 41. This other object 41 is thereupon evaluated, the respective lines of equal density being illustrated in FIG. 6. Thereafter, selection of the third object 43 is effected by means of the pulse field 42 so that finally, all three objects contained in the image field of FIG. 6 will have been evaluated individually, the substance volumes of the objects 34, 41, 43 being indicated successively as at 8.

What is claimed is:

1. In the method of measuring substance volumes in light-transmitting objects through electronic-image analysis within a field of raster-scanned subject matter, in which each scanning line lying within the boundaries of an object to be evaluated supplies by means of a discriminator a binary signal corresponding to the line length between object-boundary intercepts for the particular line, the improvement which comprises subjecting at least the object region of the field to a first frame of raster scanning at a first amplitude level of video-signal discrimination throughout said first frame scan, integrating the discriminator output signal for all scan lines between the object-boundary intercepts of said lines for said first frame, thereby developing a first integrated-frame value corresponding to the total area of the scanned object; subjecting said region to a second frame of raster scanning at a second amplitude level of video-signal discrimination throughout the second frame scan, integrating the discriminator-output signal for all scan lines between the object-boundary intercepts of said lines for said second frame, thereby developing a second integrated-frame value which corresponds to an object-scanned area that is less than said total area; developing a difference signal corresponding to the difference between said values, whereby said difference signal corresponds to the ring-like incremental area between said total area and said lesser area; multiplying said difference signal by a calibrating value which relates light-transmittance of said first ring-shaped incremental area with volume of the substance; and repeating such frame scans at successive different levels of discrimination with accompanying integration and difference-signal development and calibrating multiplication, for each of the resulting lesser ring-shaped incremental areas involved until no such incremental areas are applicable; and then adding the calibration-corrected values.

2. The method of claim 1, in which for each surface area the logarithm of the associated mean light absorption is used as the calibrating value.

3. The method of claim 1, in which the frame scanning is in television-type manner, and in which the resulting video signal is subjected to a discrimination increasing in steps by equal amounts in a direction towards higher gray values.

4. Apparatus for measuring substance volumes in light-transmitting objects through electronic-image analysis within a field of raster-scanned subject matter, comprising a field-scanning television camera, a discriminator having an input adapted to receive the video signal derived by raster-scanning in said camera and producing an output signal corresponding to the scanned line length between object-boundary intercepts for the particular line in accordance with video-signal magnitude in relation to a selected threshold value, integrating means connected to the discriminated signal for intervals corresponding to scanned-line lengths between such object-boundary intercepts, evaluation means connected to said integrating means and including a control connection to said discriminator and operative in steps of at least one raster per step to adjust the threshold value at said discriminator to progressively different values in the direction of increasing gray values; said evaluation means including (1) means differentially and correctively processing and storing the integrated signals for successively adjacent pairs of a succession of progressively discriminated rasters of scanning the object, such corrective processing being in accordance with the mean light absorption for the range between limits represented by the threshold values applicable to the integrated signals of each said pair, and (2) means for summing the stored correctively processed values; and indicating means connected to said evaluation means for indicating the value output of said summing means.

5. The apparatus of claim 4, in which said evaluation means is of the digital variety, said control connection including a digital-to analog converter.

6. The apparatus of claim 5, in which said indicating means is of the digital-display variety.

7. The apparatus of claim 5, in which said evaluation means includes selectively operable means for setting the control-signal levels applicable to successive frame-scan threshold levels at said discriminator.

8. The apparatus of claim 4, and including monitor display means connected to the output of said discriminator.

9. The apparatus of claim 4, and including selectively operable field-limiting means for selecting a single object for individual evaluation from an image field of plural objects.

10. The apparatus of claim 9, in which said discriminator is the second of two discriminators, the threshold value of the first discriminator including means for adjustably fixing the same, independent of threshold-value control of the second discriminator in successive steps via said evaluation means.

11. In the method of measuring substance volumes in light-transmitting objects through electronic-image analysis within a field of raster-scanned subject matter, in which each scanning line lying within the boundaries of an object to be evaluated supplies by means of a discriminator a binary signal corresponding to the line length between object-boundary intercepts for the particular line, the improvement which comprises subjecting at least the object region of the field to a succession of frames of raster scanning wherein there is a first amplitude level of video-signal discrimination throughout one frame scan and a second amplitude level of video-signal discrimination throughout a second and succeeding frame scan, integrating the discriminator output signal for all scan lines between the object-boundary intercepts for the first frame, integrating the discriminator output signal for all scan lines between object-boundary intercepts for the second frame, subtracting one of the integrated-frame values from the other of the integrated-frame values, and multiplying the resulting difference by a calibration factor related to a light-absorption characteristic intermediate those which correspond to the different amplitude levels selected for discrimination in the respective frames of raster scanning.

12. Apparatus for measuring substance volumes in light-transmitting objects through electronic-image analysis within a field of raster-scanned subject matter, comprising a discriminator having an input adapted to receive a video signal derived by such raster-scanning and producing a binary-signal output wherein each binary signal corresponds to the scanned line length between object-boundary intercepts for the particular line in accordance with video-signal magnitude in relation to a selected threshold value, integrating means connected to the discriminated signal corresponding to scanned-line lengths between such object-boundary intercepts, evaluation means connected to said integrating means and including a control connection to said discriminator and operative in steps of at least one raster per step to adjust the threshold value at said discriminator to progressively different values; said evaluation means including (1) means differentially and correctively processing and storing the integrated signals for successively adjacent pairs of a succession of progressively discriminated rasters of scanning the object, such corrective processing being in accordance with the mean light absorption for the range between limits represented by the threshold values applicable to the integrated signals of each said pair, and (2) means for summing the stored correctively processed values; and indicating means connected to said evaluation means for indicating the value output of said summing means.

* * * * *